May 17, 1938. J. H. NICOLAS Plant Pat. 279
ROSE
Filed June 18, 1937
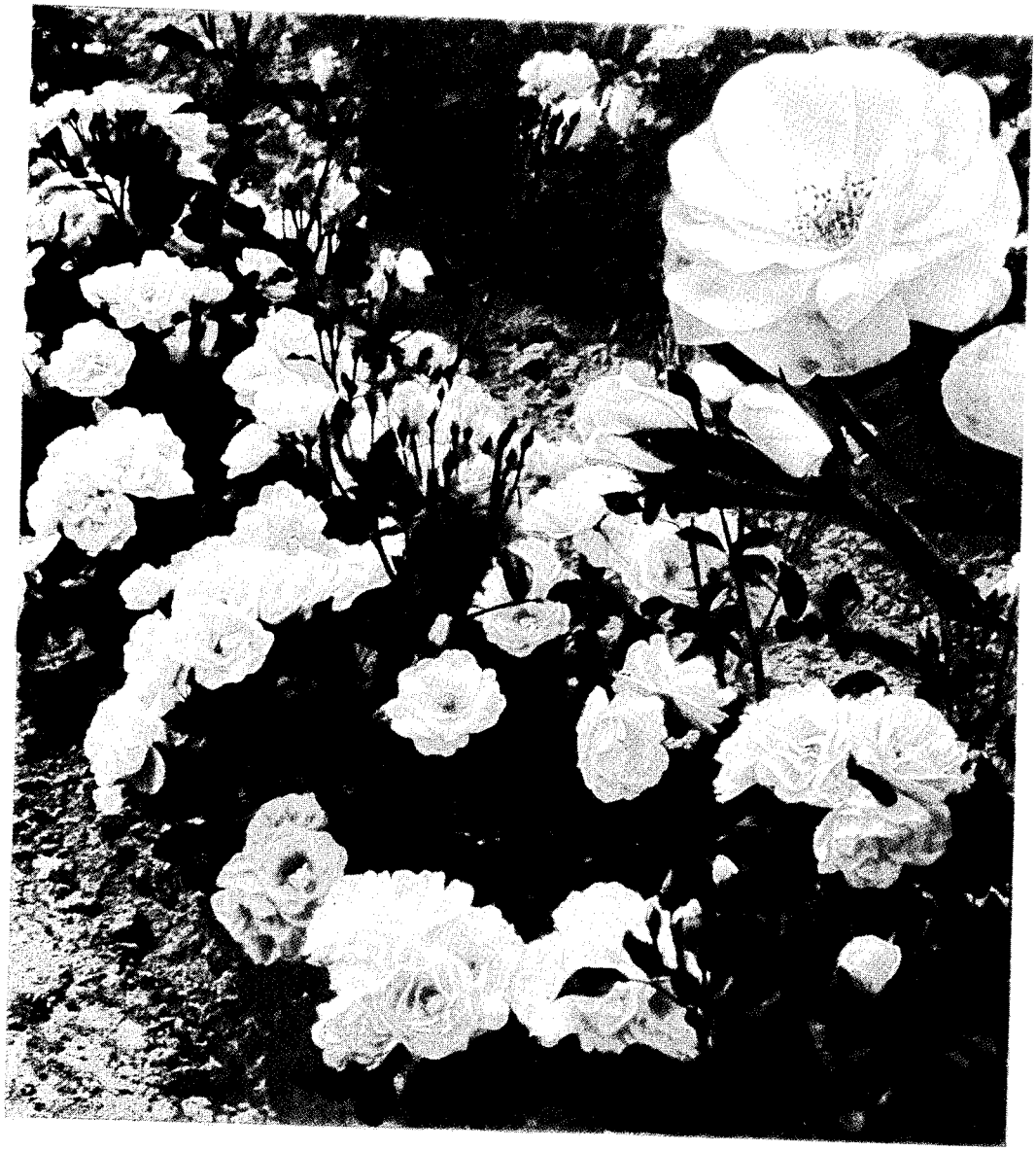
Inventor
Jean H. Nicolas
By Robb & Robb
Attorneys Patented May 17, 1938

UNITED STATES PATENT OFFICE

279

ROSE

Jean H. Nicolas, Newark, N. Y., assignor to Jackson & Perkins Company, Newark, N. Y.

Application June 18, 1937, Serial No. 149,015

1 Claim. (Cl. 47—61)

This invention relates to a new and distinct variety of large, flowering, hardy polyantha rose, the novel characteristics of which particularly adapt it for use for pleasing and permanent decorative effect in large plantings, such as mass planting in public parks and private gardens.

Hardy bedding roses of this type, often referred to as "Park Roses", have for some time been in the process of development and bid fair to become the popular rose type of the future, for which reason it was my primary object to originate such a type as herein described with the desirable attributes obtainable by the crossing of the two varieties herein named.

The new rose is one of the progeny of a cross of "Mrs. Erskine Pembroke Thom", one of the most dependable roses throughout the season, and the well known polyantha, "Gloria Mundi", both very excellent producers of flowers.

A feature of importance of this new variety is that in close mass planting each plant intertwines with the other, materially enhancing the beauty of the display. The variety is also very disease resistant and is winter hardy without protection. The plant is of medium size and branching, with glossy foliage, quite desirable factors in this type of rose.

The flowers of the present rose come in large panicles and bloom continuously throughout the season. The little buds have a buff and flesh tint which soon disappears and the flower opens into a snow-white blossom which lasts unsoiled for many days in all weather, a further advantage being apparent from this long lasting quality.

This new variety has been asexually reproduced and the distinctive characteristics have come true to form in the reproductions.

The following is a detail description of the new variety, color designations being in accordance with the Gravereaux color chart, except where obviously the ordinary dictionary definition is meant:—

Parentage:—

*Seed parent.*—Mrs. Erskine Pembroke Thom.

*Pollen parent.*—Gloria Mundi.

Classification:—

*Botanic.*—Polyantha hybrid.

*Commercial.*—Polyantha.

*Flower*

Blooming habit:—

Observations made daily in Jackson & Perkins Nurseries and test gardens.

*Recurrent.*—Continuous.

Bud:—

*Size.*—Small.

*Form.*—Urn. Unaffected by wet or hot weather.

*Color.*—When sepals first divide—Aurora. When petals begin to unfurl—Flesh. When half blown:—Inside of petals—white tinted flesh. Reverse of petals—slightly tinted flesh.

*Sepals.*—Serrated; curl back when flowers open.

*Calyx.*—Shape—funnel. Size—small. Aspect—hairy. Odor when rubbed—none.

*Peduncle.*—Length—short. Aspect—rough. Color—bronzy. Strength—stiff, slender.

*Opening.*—Bud opens well; is not affected by adverse conditions.

Bloom:—

*Size.*—Medium; average size when fully expanded 2¾''.

*Borne.*—In irregular clusters.

*Stems.*—Medium, strong.

*Form.*—When first open—cupped. Permanence—flattens.

*Petalage.*—Semi-single (two rows of petals). Number of petals under normal conditions—10 to 12.

*Color.*—Center of flower—white. Outer petals—white. Base of petals (aiglet)—lemon. Inside of petals—white. Reverse of petals—white slightly tinted flesh. General tonality from a distance—white.

*Variegations.*—None.

*Discoloration.*—No discoloration.

Petals:—

*Texture.*—Thick; unaffected by wet or hot weather.

*Appearance.*—Inside and outside, satiny.

*Form.*—Round.

*Arrangement.*—Imbricated (regularly arranged shinglelike). Petaloids in center—none.

*Persistence.*—Drop off cleanly.

*Fragrance.*—Slight. Nature—Sweet briar.

*Lasting quality.*—On the plant and as cut flower, very long.

Genital organs:—

*Stamens, anthers.*—Small many. Color—yellow. Arrangement—regular around styles.

*Stamens, filaments (threads).*—Medium. Color—white.

*Pollen.*—White.

*Styles.*—Bunched, even length; short, heavy.

*Stigmas.*—White.

*Ovaries.*—All enclosed in calyx.

Fruit:—
Variety is fertile with its own pollen.
*Form.*—Round.
*Aspect.*—Rough.
*Color at maturity.*—Scarlet.
*Sepals.*—Caducous.

*Plant*

Form:—
Bush.
Growth:—
Medium, branching.
Foliage:—
Generally seven leaflets.
*Size.*—Medium.
*Quantity.*—Abundant.
*Color.*—New foliage—light green. Old foliage:—Upper side—normal green. Under side—lighter green.
*Shape.*—Oval pointed.
*Texture.*—Upper side—glossy. Under side—smooth. Ribs and veins—ordinary.
*Edge.*—Serrated.
*Serration.*—Single, small.
*Rachis.* — Color — reddish. Under side—prickles.
*Stipules.*—Medium length, bearded.
*Disease resistance.*—Resistant.
Wood:—
*New wood.*—Color—reddish. Bark—rough.
*Old wood.*—Color—green. Bark—rough.
Thorns: (Divided into thorns, prickles and short needles):—
*Thorns.*—Quantity: On main stalks from base—ordinary. On laterals from stalk—few. Form—broad base, medium, hooked downward. Color when young—red. Position—irregular.
*Prickles.*—Quantity: On main stalks—few. On laterals—none. Color—brown.
*Short needles.*—None.

I claim:

A new variety of large, flowering, hardy polyantha rose particularly adapted for mass planting, characterized by its intertwining characteristics, its disease resistance and winter hardiness, and the snow-white coloring and long lasting qualities of its flowers, substantially as shown and described.

JEAN H. NICOLAS.